US009266871B2

(12) United States Patent
Follmann et al.

(10) Patent No.: US 9,266,871 B2
(45) Date of Patent: Feb. 23, 2016

(54) TRIFLUOROMETHYL-SUBSTITUTED FUSED PYRIMIDINES AND THEIR USE

(71) Applicant: BAYER PHARMA AKTIENGESELLSCHAFT, Berlin (DE)

(72) Inventors: Markus Follmann, Köln (DE); Johannes-Peter Stasch, Solingen (DE); Gorden Redlich, Bochum (DE); Dieter Lang, Velbert (DE); Alexandros Vakalopoulos, Hilden (DE); Frank Wunder, Wuppertal (DE); Adrian Tersteegen, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/194,224

(22) Filed: Feb. 28, 2014

(65) Prior Publication Data

US 2014/0249168 A1    Sep. 4, 2014

(30) Foreign Application Priority Data

Mar. 1, 2013    (EP) .................................... 13157434

(51) Int. Cl.
| | | |
|---|---|---|
| A01N 43/90 | (2006.01) |
| A61K 31/519 | (2006.01) |
| C07D 487/00 | (2006.01) |
| C07D 417/04 | (2006.01) |
| A61K 45/06 | (2006.01) |
| C07D 519/00 | (2006.01) |

(52) U.S. Cl.
CPC ............ *C07D 417/04* (2013.01); *A61K 31/519* (2013.01); *A61K 45/06* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 5,976,523 A | 11/1999 | Awaya et al. |
| 6,180,656 B1 | 1/2001 | Fürstner et al. |
| 6,451,805 B1 | 9/2002 | Straub et al. |
| 6,743,798 B1 | 6/2004 | Straub et al. |
| 6,833,364 B1 | 12/2004 | Straub et al. |
| 6,903,089 B1 | 6/2005 | Stasch et al. |
| 7,173,037 B2 | 2/2007 | Alonso-Alija et al. |
| 7,410,973 B2 | 8/2008 | Feurer et al. |
| 7,414,136 B2 | 8/2008 | Matsumura et al. |
| 8,242,272 B2 | 8/2012 | Jimenez et al. |
| 8,309,551 B2 | 11/2012 | Schirok et al. |
| 8,420,656 B2 | 4/2013 | Follmann et al. |
| 2004/0235863 A1 | 11/2004 | Feurer et al. |
| 2011/0218202 A1 | 9/2011 | Brockunier et al. |
| 2013/0072492 A1 | 3/2013 | Raghavan et al. |
| 2013/0172372 A1 | 7/2013 | Follmann et al. |
| 2013/0178475 A1 | 7/2013 | Moore et al. |
| 2013/0210824 A1 | 8/2013 | Follmann et al. |
| 2013/0338137 A1 | 12/2013 | Follmann et al. |
| 2014/0100229 A1 | 4/2014 | Follmann et al. |
| 2014/0148433 A1 | 5/2014 | Follmann et al. |
| 2014/0350020 A1 | 11/2014 | Follmann et al. |
| 2014/0357637 A1 | 12/2014 | Follmann et al. |
| 2015/0025090 A1 | 1/2015 | Follmann et al. |
| 2015/0065533 A1 | 3/2015 | Follmann et al. |
| 2015/0080414 A1 | 3/2015 | Follmann et al. |
| 2015/0094308 A1 | 4/2015 | Follmann et al. |
| 2015/0274754 A1 | 10/2015 | Follmann et al. |

FOREIGN PATENT DOCUMENTS

| | | |
|---|---|---|
| CA | 2804470 | 1/2012 |
| CA | 2809911 | 3/2012 |
| CA | 2834901 | 11/2012 |
| CA | 2840886 | 1/2013 |
| CN | 1613849 | 5/2005 |
| EP | 0634413 | 1/1995 |
| WO | 0183490 | 11/2001 |
| WO | 0259083 | 8/2002 |
| WO | 2011161099 | 12/2011 |
| WO | 2012152629 | 5/2012 |
| WO | 2013030138 | 3/2013 |
| WO | 2013104597 | 7/2013 |

OTHER PUBLICATIONS

Becker et al.,"NO-Independent Regulatory Site of Direct sGC Stimulators like YC-1 and Bay 41-2272," BMC Pharmacology, 2001, 1: 13.
Cheng et al.,"Potential Purine Antagonists VII. Synthesis of 6-Alkylpyrazolo-[3,4-d]pyrimidines," J. Org. Chem., 1958, 23:191-200.
Evgenov et al.,"NO-independent stimulators and activators of soluble guanylate cyclase: discovery and therapeutic potential," Nat. Rev. Drug. Disc, Sep. 2006, 5:755-768.
Glass et al., "Stimulation of Human Platelet Guanylate Cyclase by Fatty Acids," J. Biol. Chem., Feb. 25, 1977, 252(4):1279-1285.
Hassan et al.,"Aryl-Aryl Bond Formation One Century after the Discovery of the Ullmann Reaction," Chem. Rev. 2002, 102: 1359-1469.
Ko et al., "YC-1, a Novel Activator of Platelet Guanylate Cyclase," Blood, Dec. 1994, 84(12): 4226-4233.
Kozo, O., International Review of Experimental Pathology, University of Bristol Medical School, Bristol, England, "Spontaneous Hypertension in Rats," 1969, 7:227-270.

(Continued)

*Primary Examiner* — Jeffrey H Murray
(74) *Attorney, Agent, or Firm* — Buchanan Ingersoll & Rooney

(57) ABSTRACT

The present application relates to novel trifluoromethyl-substituted fused pyrimidines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

17 Claims, No Drawings

(56) References Cited

OTHER PUBLICATIONS

Maarten van den Buuse,"Circadian Rythyms of Blood Pressure, Heart Rate, and Locomotor Activity in Spontaneously Hypertensive Rats as Measured with Radio-Telemetry," Physiology & Behavior, 1994, 55(4):783-787.
Mittendorf et al., "Discovery of Riociguat (BAY 63/2521): A Potent, Oral Stimulator of Soluble Guanylate Cyclase for the Treatment of Pulmonary Hypertension," Chem. Med. Chem., 2009, 4: 853-865.
Mülsch et al., "Effect of YC-1, an NO-independent, superoxide-sensitive stimulator of soluble guanylyl cyclase, on smooth muscle responsiveness to nitrovasodilators," Brit. J. Pharm., 1997, 120:681-689.
Palacios et al. "A New and Efficient Synthesis of Imidazo[1,5-a]pyridine Derivatives by a Tandem Aza-Wittig/Electrocyclic Ring Closure of N-vinylic phosphazenes," Tetrahedron, 1995, 51(12): 3683-3690.
Pettibone et al., "A Structurally Novel Stimulator of Guanylate Cyclase with Long-Lasting Hypotensive Activity in the Dog," Euro. J. of Pharmacology, 1985, 116: 307-312.
Saenz de Tejada et al., Int J of Impotence Res 2001, 13:282- 290.
Sharkovska et al.,"Nitric oxide-independent stimulation of soluble guanylate cyclase reduces organ damage in experimental low-renin and high-renin models," J. Hypertnesion, 2010, 28(8):1666-1675.
Stasch et al.,"Soluble Guanylate Cyclase as an Emerging Therapeutic Target in Cardiopulmonary Disease," Circulation, May 2011, 123: 2263-2273.
Straub et al., "NO-Independent Stimulators of Soluble Guanylate Cyclase," Bioorg. Med. Chem. Lett., 2001, 11:781-784.
Tyutin et al., "Synthesis of Esters of 3,3-Dicyano-2-(Trifluoromethyl) Acrylic Acid and Their Reactions With Arylamines" Journal of Fluorine Chemistry, 1991, 51:323-334.
Wilson et al.,"Development of a Scaleable Synthesis of a Partial Nicotinic Acid Receptor Agonist," Organic Process Research & Development, 2009, 13: 543-547.
Winn et al., "2-(Alkylamino)nicotinic Acid and Analogs. Potent Angiotensin II Antagonists," J. Med. Chem 1993, 36: 2676-2688.
Witte et al.,"Experimental heart failure in rats: effects on cardiovascular circadian rhythms and on myocardial β-adrenergic signaling," Cardiovascular Research, 2000, 47: 350-358.
Wu et al., "YC-1 inhibited human platelet aggregation through NO-independent activation of soluble guanylate cyclase," Br J. Pharmacol. Oct. 1995, 116(3):1973-1978.
Wunder et al., "A cell-based cGMP assay useful for ultra-high-throughput screening and identification of modulators of the nitric oxide/cGMP pathway," Anal. Biochem., 2005, 339:104-112.
Wunder et al., "Characterization of the First Potent and Selective PDE9 Inhibitor Using a cGMP Reporter Cell Line," Molecular Pharmacology 2005, vol. 68, No. 6, 1775-1781.
Yu et al., "Vasorelaxant Effect of Isoliquiritigenin, A novel soluble guanylate cyclase activator, in rat aorta," Brit. J. of Pharmacology, 1995, 114: 1587-1594.
U.S. Appl. No. 13/144,929, 371(c) date Dec. 23, 3012.
U.S. Appl. No. 14/115870, 371(c) date Feb. 5, 2014.
U.S. Appl. No. 14/131,017, 371(c) date Feb. 27, 2014.
U.S. Appl. No. 13/736,692, filed Jan. 8, 2013.
U.S. Appl. No. 13/599,975, filed Aug. 30, 2012.
Badesch et al., "Prostanoid Therapy for Pulmonary Arterial Hypertension," Journal of the American College of Cardiology, Jun. 16, 2004, 43:56S-61S.
Ghofrani et al., "Soluble guanylate cyclase stimulation: an emerging option in pulmonary hypertension therapy," Eur. Respir. Rev., 2009, 18(111):35-41.
Freshney, R. Ian., "Culture of animal cells," A Manual of Basic Technique, Alan R. Liss, Inc., 1983, New York, p. 4.
Dermer, G. B., "Another Anniversary for the War on Cancer," Bio/Technology, 1994, 12:320.
Oudot et al., "Combination of BAY 60-4552 and Vardenafil Exerts Proerectile Facilitator Effects in Rats With Cavernous Nerve Injury: A Proof of Concept Study for the Treatment of Phosphodiesterase Type 5 Inhibitor Failure," European Urology, 2011, 60:1020-1026.
Dumitrascu et al., "Activation of Soluble Guanylate Cyclase Reverses Experimental Pulmonary Hypertension and Vascular Remodeling," 113(2) Circulation 286, 286-95 (Jan. 2006).
Hackam, et al. "Translation of Research Evidence from Animals to Humans," JAMA, 296(14), 2006, 1731-1732.
Hobbs, "Soluble guanylate cyclase: an old therapeutic target revisited," 136 British J. Pharmacology 637, 637-40 (2002).
T.A. Michel, "Treatment of Myocardial Ischemia," in Goodman & Gilman's: The Pharmacological Basis of Therapeutics, 823-844 (L.L. Brunton et al., eds. 11th ed., 2006).
Olah et al., "Synthesis and Investigation of Organic Fluorine Compounds. XXIII. Preparation of Aromatic Fluorinated Esters as Local Anesthetics," J. Organic Chem. 1957, vol. 22, pp. 879-881.
Poulos, "Soluble Guanylate Cyclase," Current Opinion in Structural Biology, 736-743 (2006).
U.S. Appl. No. 14/771,542, filed Aug. 31, 2015.

TRIFLUOROMETHYL-SUBSTITUTED FUSED PYRIMIDINES AND THEIR USE

The present application relates to novel trifluoromethyl-substituted fused pyrimidines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. This is of central importance for the activation mechanism. NO can bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the abovementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attack at the central iron atom of haem. In addition to the side effects, the development of tolerance is one of the decisive disadvantages of this type of treatment.

Some years ago, a number of substances were described which stimulate soluble guanylate cyclase directly, i.e. without prior release of NO, such as, for example, 3-(5'-hydroxymethyl-2'-furyl)-1-benzylindazole [YC-1; Wu et al., *Blood* 84 (1994), 4226; Mülsch et al., *Brit. J. Pharmacol.* 120 (1997), 681]. The more recent stimulators of soluble guanylate cyclase include among others BAY 41-2272, BAY 41-8543 and riociguat (BAY 63-2521) (see, for example, Stasch J.-P. et al., *Nat. Rev. Drug Disc.* 2006; 5: 755-768; Stasch J.-P. et al., *Chem Med Chem* 2009; 4: 853-865. Stasch J.-P. et al., *Circulation* 2011; 123: 2263-2273).

As stimulators of soluble guanylate cyclase, WO 00/06568 and WO 00/06569 disclose fused pyrazole derivatives, and WO 03/095451 discloses carbamate-substituted 3-pyrimidinylpyrazolopyridines. 3-Pyrimidinylpyrazolopyridines with phenylamide substituents are described in E. M. Becker et al., *BMC Pharmacology* 1 (13), 2001. WO 2004/009590 describes pyrazolopyridines with substituted 4-aminopyrimidines for treatment of CNS disorders. WO 2010/065275 and WO 2011/149921 disclose substituted pyrrolo- and dihydropyridopyrimidines as sGC activators. As sGC stimulators, WO 2012/004259 describes fused aminopyrimidines, and WO 2012/004258, WO 2013/004785 and WO 2013/030288 describe fused pyrimidines and triazines. WO 2012/28647 discloses pyrazolopyridines with various azaheterocycles for treatment of cardiovascular disorders.

It was an object of the present invention to provide novel substances which act as stimulators of soluble guanylate cyclase and which have an identical or improved therapeutic profile compared to compounds known from the prior art, for example with respect to their in vivo properties such as their pharmacokinetic and pharmacodynamic behaviour and/or their metabolic profile and/or their dose-activity relationship and/or their side effect profile.

The present invention provides the compound having the systematic name 2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and the structural formula (I)

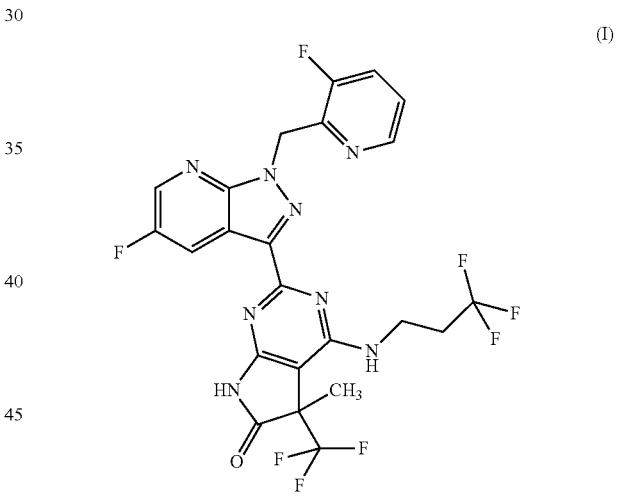

and the N-oxides, salts, solvates, salts of the N-oxides and solvates of the N-oxides and salts thereof.

Compounds according to the invention are the compounds of the formulae (I), (I-A) and (1-B) and their salts, solvates and solvates of the salts, the compounds, comprised by formulae (I), (I-A) and (I-B), of the formulae mentioned below and their salts, solvates and solvates of the salts and the compounds comprised by formulae (I), (I-A) and (I-B), mentioned below as embodiments, and their salts, solvates and solvates of the salts, if the compounds, comprised by formulae (I), (I-A) and (I-B), mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of the solvates in which the coordination is with water. Preferred solvates in the context of the present invention are hydrates.

The compounds according to the invention can exist in different stereoisomeric forms, that is in the form of configurational isomers. The present invention therefore encompasses the enantiomers and their mixtures. The stereoisomerically uniform constituents can be isolated from such mixtures of enantiomers in a known manner; chromatography processes are preferably used for this, in particular HPLC chromatography on a chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^{3}H$ or $^{14}C$ isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

In the context of the present invention, preference is given to the enantiomer of the compound (I) having the systematic name (5R)-2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and the structural formula (I-A)

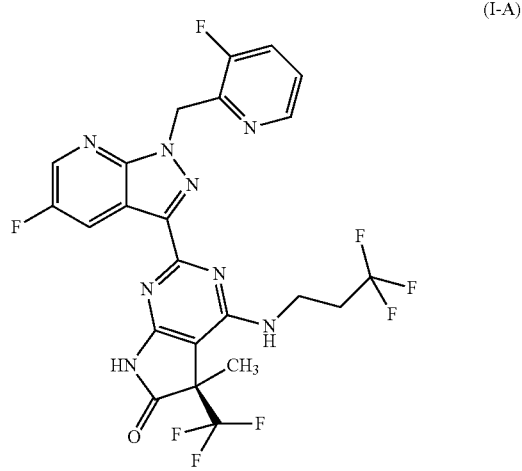 [SMILES: C[C@]1(C(F)(F)F)C(=O)Nc2nc(-c3nn(Cc4ncccc4F)c4ncc(F)cc34)nc(NCCC(F)(F)F)c21]

(I-A)

and the salts, solvates and solvates of the salts thereof.

In the context of the present invention, preference is given to the enantiomer of the compound (I) having the systematic name (5S)-2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and the structural formula (I-B)

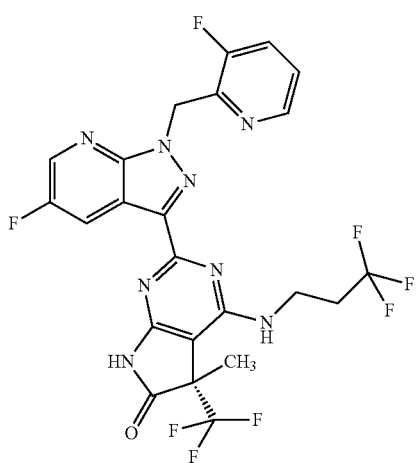
(I-B)

and the salts, solvates and solvates of the salts thereof.

The invention furthermore provides a process for preparing the compounds of the formula (I) according to the invention, characterized in that a compound of the formula (II)

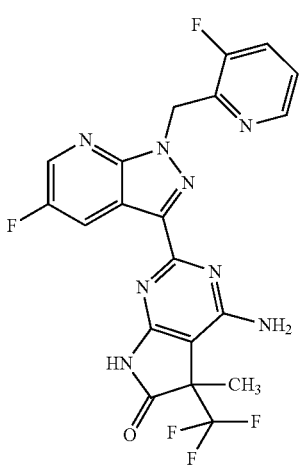
(II)

is converted in an inert solvent using isopentyl nitrite and a halogen equivalent into a compound of the formula (III)

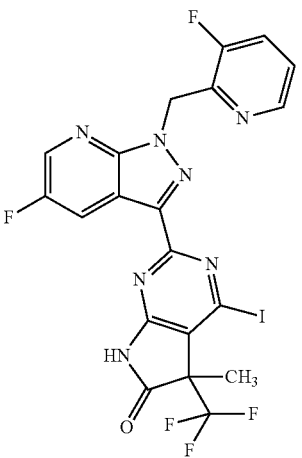
(III)

and this is then reacted in an inert solvent, optionally in the presence of a suitable base, with a compound of the formula (IV)

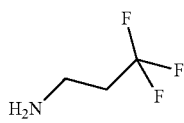
(IV)

to give the compound of the formula (I)

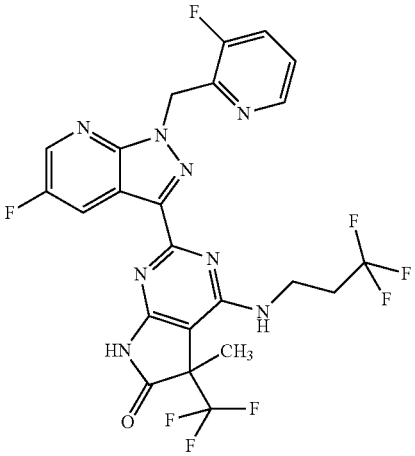
(I)

and the resulting compound of the formula (I) is optionally converted with the appropriate (i) solvents and/or (ii) acids or bases to the solvates, salts and/or solvates of the salts thereof.

Process step (II)→(III) is carried out with or without solvent. Suitable solvents are all organic solvents which are inert under the reaction conditions. The preferred solvent is dioxane.

The reaction (II)→(III) is generally carried out in a temperature range of from +20° C. to +100° C., preferably within the range from +50° C. to +100° C., optionally in a microwave. The reaction can be carried out at atmospheric, elevated or reduced pressure (for example in the range from 0.5 to 5 bar). In general, atmospheric pressure is employed.

Suitable halogen sources in the reaction (II)→(III) are, for example, diiodomethane, a mixture of caesium iodide, iodine and copper(I) iodide or copper(II) bromide.

Inert solvents for the process step (III)+(IV)→(I) are, for example, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to NMP.

The reaction (III)+(IV)→(I) is generally conducted within a temperature range of +20° C. to +200° C., preferably at +150° C. to +200° C., preferably in a microwave. The reaction can be carried out at atmospheric, elevated or reduced pressure (for example from 0.5 to 5 bar).

The preparation process described can be illustrated by the synthesis scheme below (Scheme 1):

Scheme 1

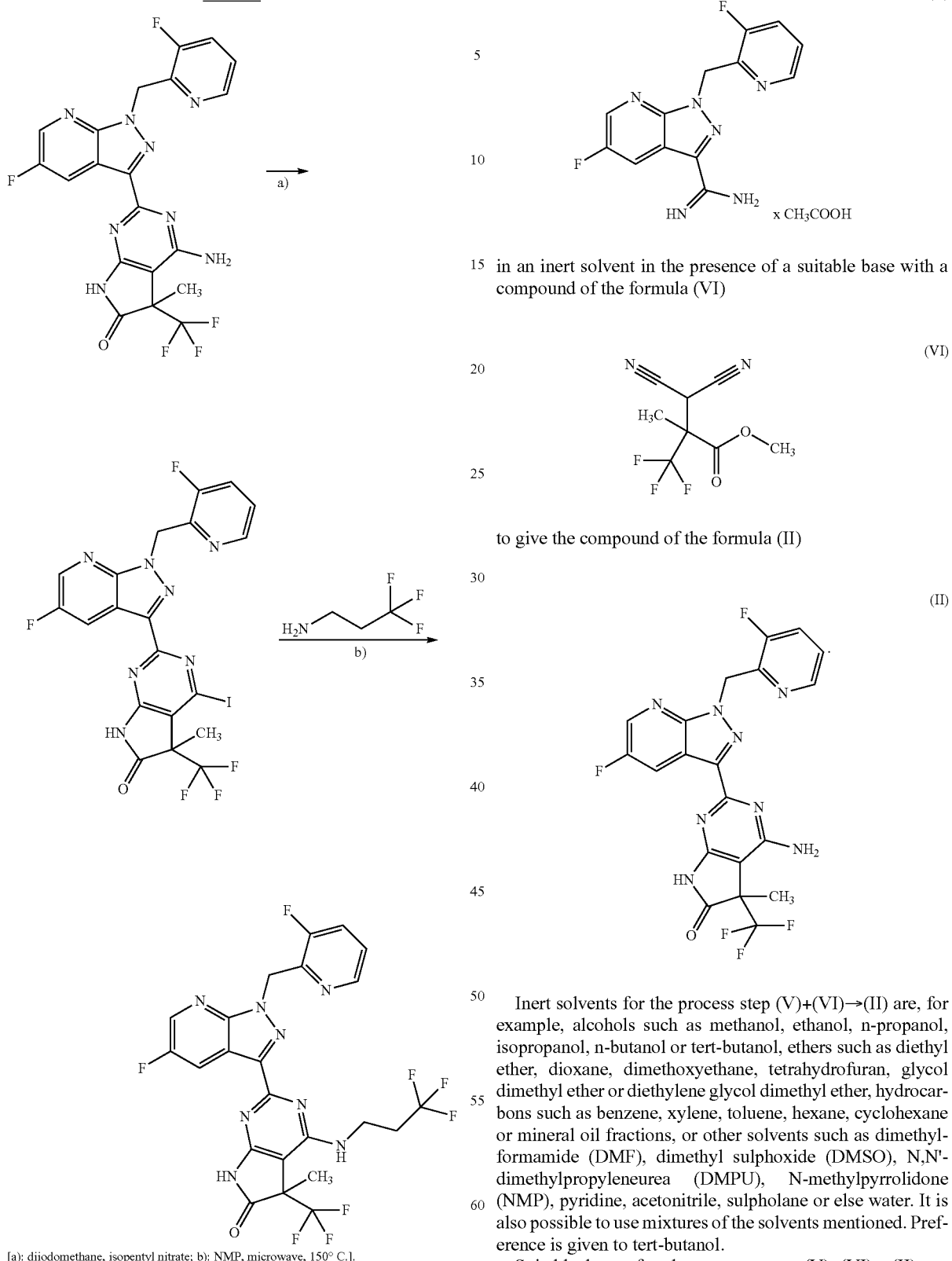

[a]: diiodomethane, isopentyl nitrate; b): NMP, microwave, 150° C.].

The compounds of the formula (II) can be prepared by reacting a compound of the formula (V)

in an inert solvent in the presence of a suitable base with a compound of the formula (VI)

to give the compound of the formula (II)

Inert solvents for the process step (V)+(VI)→(II) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile, sulpholane or else water. It is also possible to use mixtures of the solvents mentioned. Preference is given to tert-butanol.

Suitable bases for the process step (V)+(VI)→(II) are alkali metal hydroxides such as, for example, lithium hydroxide, sodium hydroxide or potassium hydroxide, alkali metal carbonates such as lithium carbonate, sodium carbonate, potassium carbonate or caesium carbonate, alkali metal bicarbonates such as sodium bicarbonate or potassium bicarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo [5.4.0]undec-7-ene (DBU) or 1,5-diazabicyclo[4.3.0]non-5-ene (DBN). Preference is given to potassium tert-butoxide.

The reaction (V)+(VI)→(II) is generally conducted within a temperature range of +20° C. to +150° C., preferably at +75° C. to +100° C., optionally in a microwave. The reaction can be carried out at atmospheric, elevated or reduced pressure (for example from 0.5 to 5 bar). In general, atmospheric pressure is employed.

The preparation process described above can be illustrated in an exemplary manner by the synthesis scheme below (Scheme 3):

Scheme 3

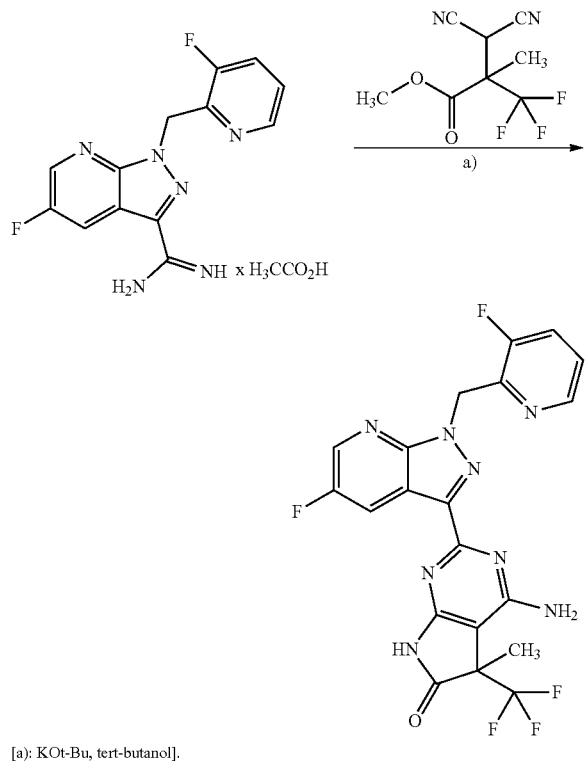

[a]: KOt-Bu, tert-butanol].

The compounds of the formula (V) are known from the literature (see, for example, WO 2013/004785, example 14A).

The compound of the formula (VI) can be prepared by reacting a compound of the formula (VII)

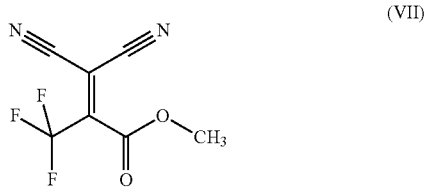

(VII)

in an inert solvent with methylmagnesium halide.

The compound of the formula (VII) is known from the literature (cf., for example, Journal of Fluorine Chemistry, 1991, vol. 51, #3 pp. 323-334).

The compound of the formula (IV) is commercially available, known from the literature or can be prepared in analogy to literature processes.

The compounds according to the invention act as potent stimulators of soluble guanylate cyclase, have valuable pharmacological properties and have an improved therapeutic profile, for example with respect to the in vivo properties thereof and/or the pharmacokinetic characteristics and/or metabolic profile thereof. They are therefore suitable for the treatment and/or prophylaxis of diseases in humans and animals.

The compounds according to the invention cause vasorelaxation and inhibition of platelet aggregation, and lead to a decrease in blood pressure and to a rise in coronary blood flow. These effects are mediated via direct stimulation of soluble guanylate cyclase and intracellular cGMP increase. Moreover, the compound according to the invention enhances the effect of substances increasing the cGMP concentration, such as, for example, EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, hypertension, resistant hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term "heart failure" encompasses both acute and chronic forms of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the compound according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity and of combined hyperlipidaemias and metabolic syndrome.

The compounds according to the invention can additionally be used for the treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic overactive bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds according to the invention are furthermore suitable for the treatment and/or prophylaxis of kidney disorders, in particular of acute and chronic renal insufficiency and acute and chronic renal failure. In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions on glomerulae and arterioles, tubular dilatation, hyperphosphataemia and/or need for dialysis. The present invention also encompasses the use of the compounds according to the invention for the treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinisation, multiple sclerosis, thalamic degeneration, Creutzfeld-Jacob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

Furthermore, the compounds according to the invention are also suitable for regulating cerebral blood flow and are thus effective agents for control of migraine. They are also suitable for prophylaxis and control of sequelae of cerebral infarction (cerebral apoplexy) such as stroke, cerebral ischaemia and craniocerebral trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarkoidosis).

The compounds according to the invention are furthermore suitable for controlling postoperative scarring, for example as a result of glaucoma operations.

The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides for the use of the compounds according to the invention for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds according to the invention for use in a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds according to the invention for production of a medicament for the treatment and/or prophylaxis of disorders, especially of the aforementioned disorders.

The present invention further provides for the use of the compounds according to the invention for producing a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds according to the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active ingredient combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, in particular PDE 5 inhibitors such as sildenafil, vardenafil and tadalafil;

agents having antithrombotic activity, for example and with preference from the group of platelet aggregation inhibitors, of anticoagulants or of profibrinolytic substances;

active compounds lowering blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or active compounds altering lipid metabolism, for example and with preference from the group of thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, dabigatran, melagatran, bivalirudin or clexane.

In a preferred embodiment of the invention, the compounds according to the invention are administered in combination with a GPIIb/IIIa antagonist such as, by way of example and with preference, tirofiban or abciximab.

In a preferred embodiment of the invention, the compounds according to the invention are administered in combination with a factor Xa inhibitor, by way of example and with preference rivaroxaban (BAY 59-7939), edoxaban (DU-176b), apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a loop diuretic such as, for example, furosemide, torasemide, bumetanide and piretanide, with potassium-sparing diuretics such as, for example, amiloride and triamterene, with aldosterone antagonists such as, for example, spironolactone, potassium canrenoate and eplerenone and also thiazide diuretics such as, for example, hydrochlorothiazide, chlorthalidone, xipamide and indapamide.

Agents which modify lipid metabolism are preferably understood to mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds according to the invention are administered in combination with a CETP inhibitor, by way of example and with preference dalcetrapib, BAY 60-5521, anacetrapib oder CETP vaccine (CETi-1).

In a preferred embodiment of the invention, the compounds according to the invention are administered in combination with a thyroid receptor agonist, by way of example and with preference D-thyroxin, 3,5,3'-triiodothyronin (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or ITT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, a preferred example being orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT(=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, non-toxic, pharmaceutically suitable auxiliaries, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Administration forms which function according to the prior art, release the compounds according to the invention rapidly and/or in a modified manner and contain the compounds according to the invention in crystalline and/or amorphized and/or dissolved form are suitable for oral administration, such as e.g. tablets (non-coated or coated tablets, for example with enteric coatings or coatings that dissolve in a delayed manner or are insoluble and control the release of the compound according to the invention), tablets or films/oblates, films/lyophilisates or capsules which disintegrate rapidly in the oral cavity (for example hard or soft gelatine capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilisates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be accomplished in a manner known per se by mixing with inert, non-toxic, pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctors.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The working examples which follow illustrate the invention.

The percentages in the tests and examples which follow are, unless indicated otherwise, percentages by weight; parts are parts by weight. Solvent ratios, dilution ratios and concentration figures for liquid/liquid solutions are each based on volume.

A. EXAMPLES

Abbreviations and Acronyms

DCI direct chemical ionization (in MS)
DMF dimethylformamide
DMSO dimethyl sulphoxide
ESI electrospray ionization (in MS)
h hour(s)
HPLC high-pressure, high-performance liquid chromatography
LC/MS liquid chromatography-coupled mass spectrometry
min minute(s)
MS mass spectrometry
NMR nuclear magnetic resonance spectrometry
RT room temperature
$R_t$ retention time (in HPLC)
t-Bu tert-butyl
TFA trifluoroacetic acid
THF tetrahydrofuran
v/v ratio by volume (of a solution)
HPLC and LC/MS Methods:
Method 1 (LC-MS):
Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

If, in the synthesis intermediates and working examples of the invention described below, a compound is given in the form of a salt of the corresponding base or acid, the exact stoichiometric composition of such a salt as obtained by the respective preparation and/or purification process is generally not known. Unless specified in more detail, additions to names and structural formulae, such as "hydrochloride", "trifluoroacetate", "sodium salt" or "x HCl", "x CF$_3$COOH", "x Na$^+$" are not to be understood stoichiometrically in the case of such salts, but have only descriptive character with regard to the salt-forming components comprised therein.

This applies correspondingly if the synthesis intermediates and working examples or salts thereof were obtained by the preparation and/or purification processes described in the form of solvates, for example hydrates, whose stoichiometric composition (if of a defined type) is not known.

Starting Materials and Intermediates:

Example 1A

5-Fluoro-1-[(3-fluoropyridin-2-yl)methyl]-1H-pyrazolo[3,4-b]pyridine-3-carboximidamide acetate

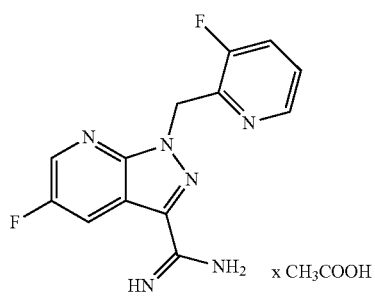 [SMILES: N=C(N)c1nn(Cc2ncccc2F)c2ncc(F)cc12]

The preparation of the compound is described in WO2013/004785, example 14A, pp. 69-70.

Example 2A

Methyl 3,3-dicyano-2-(trifluoromethyl)acrylate

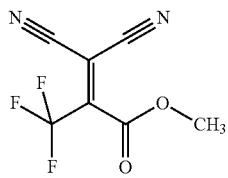

The synthesis of this compound is described in Journal of Fluorine Chemistry, 1991, vol. 51, #3 pp. 323-334.

Example 3A

Methyl 2-(dicyanomethyl)-3,3,3-trifluoro-2-methyl-propanoate

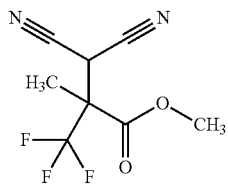

3.00 g (14.698 mmol) of Example 2A were dissolved in tetrahydrofuran (30 ml) and the solution was cooled to 0° C. 7.35 ml (22.047 mmol) of methylmagnesium chloride (3M in THF) were then added dropwise such that the temperature did not exceed 5° C. After the addition had ended, the mixture was stirred for another 10 min. 1N aqueous hydrochloric acid was then added to the reaction, and the mixture was subsequently extracted with ethyl acetate. The phases were separated and the aqueous phase was extracted two more times with ethyl acetate. The combined organic phases were washed with saturated aqueous sodium chloride solution, dried over sodium sulphate, filtered and concentrated. The crude product was then chromatographed on silica gel (mobile phase: cyclohexane, then cyclohexane:ethyl acetate 9:1 (v:v)). Concentration gave 3.24 g (63% of theory) of the title compound.

$^1$H-NMR (400 MHz, CDCl$_3$): δ [ppm]=1.81 (s, 3H), 3.95 (s, 3H), 4.48 (s, 1H).

Example 4A

4-Amino-2-{5-fluoro-1-[(3-fluoropyridin-2-yl)methyl]-1H-pyrazolo[3,4-b]pyridin-3-yl}-5-methyl-5-(trifluoromethyl)-5,7-dihydro-6H-pyrrolo[2,3-d]pyrimidin-6-one

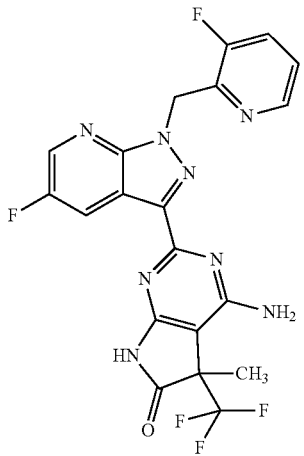

23.0 g (66.023 mmol) of Example 1A were initially charged in tert-butanol (400 ml), and 13.43 g (119.683 mmol) of potassium tert-butoxide were added. Subsequently, 21.079 g (95.746 mmol) of Example 3A in tert-butanol (100 ml) were added and the mixture was heated at reflux overnight. After cooling, water was added and the reaction mixture was stirred at room temperature for 30 min. The precipitate formed was filtered off and washed with water and a little diethyl ether. The solid was dried under high vacuum. This gave 16.1 g of the title compound (51% of theory).

LC-MS (Method 1): R$_t$=0.95 min; MS (ESIpos): m/z=477 [M+H]$^+$ $^1$H-NMR (400 MHz, DMSO-d$_6$): δ [ppm]=1.72 (s, 3H), 5.96 (s, 2H), 7.10 (br s, 2H), 7.42-7.48 (m, 1H), 7.75-7.80 (m, 1H), 8.27 (d, 1H), 8.68 (dd, 1H), 8.86 (dd, 1H), 11.60 (br s, 1H).

Example 5A

2-{5-Fluoro-1-[(3-fluoropyridin-2-yl)methyl]-1H-pyrazolo[3,4-b]pyridin-3-yl}-4-iodo-5-methyl-5-(trifluoromethyl)-5,7-dihydro-6H-pyrrolo[2,3-d]pyrimidin-6-one

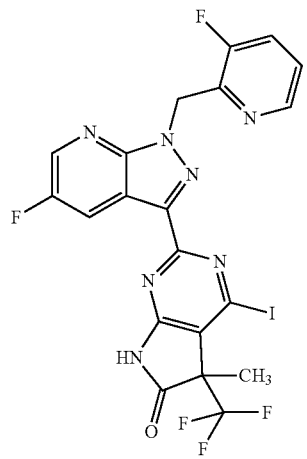 [SMILES: CC1(C(F)(F)F)C(=O)Nc2nc(-c3nn(Cc4ncccc4F)c4ncc(F)cc34)nc(I)c21]

798 µl (5.930 mmol) of isopentyl nitrite and 286 µl (3.558 mmol) of diiodomethane were added to 565 mg (1.186 mmol) of Example 4A in dioxane (15 ml), and the mixture was heated at 85° C. for 4 h. After cooling, the mixture was concentrated under reduced pressure, the residue was taken up in dichloromethane, kieselguhr was added and the mixture was then concentrated under reduced pressure. The crude compound adsorbed on kieselguhr was then chromatographed on silica gel (mobile phase: cyclohexane:ethyl acetate gradient). Concentration gave 297 mg (42% of theory) of the title compound.

LC-MS (Method 1): R$_t$=1.19 min; MS (ESIpos): m/z=588 [M+H]$^+$

¹H-NMR (400 MHz, DMSO-d₆): δ [ppm]=1.81 (s, 3H), 6.04 (s, 2H), 7.43-7.47 (m, 1H), 7.77-7.82 (m, 1H), 8.26 (d, 1H), 8.47 (dd, 1H), 8.76 (dd, 1H), 12.41 (br s, 1H).

WORKING EXAMPLES

Example 1

2-{5-Fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one

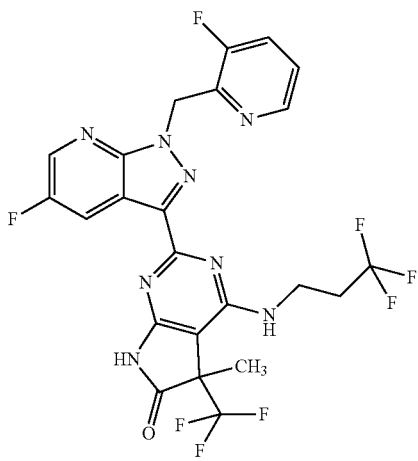 [SMILES: CC1(C(F)(F)F)C(=O)Nc2nc(-c3nn(Cc4ncccc4F)c4ncc(F)cc34)nc(NCCC(F)(F)F)c21]

In a microwavable reaction vessel, 293 mg (0.462 mmol, purity about 92%) of Example 5A were dissolved in 1-methyl-2-pyrrolidone (4.5 ml), and 126 µl (1.409 mmol) of 3,3,3-trifluoropropyl-1-amine were added. The vessel was then sealed with a septum and heated at 150° C. in the microwave for 3 h. After cooling, the reaction mixture was purified by preparative HPLC (acetonitrile:water (+0.05% formic acid) gradient). This gave 168 mg of the title compound (62% of theory, purity 97%).

LC-MS (Method 1): R$_t$=1.15 min; MS (EIpos): m/z=573 [M+H]⁺.

¹H NMR (400 MHz, DMSO-d₆): δ [ppm]=1.73 (s, 3H), 2.64-2.71 (m, 2H), 3.79-3.93 (m, 2H), 5.99 (s, 2H), 6.91 (t, 1H), 7.42-7.46 (m, 1H), 7.78 (t, 1H), 8.28 (d, 1H), 8.46 (dd, 1H), 8.71 (s br, 1H), 11.71 (br s, 1H).

Separation into Enantiomers:

301 mg of racemate (combined amount Example 1 from 2 different batches) were separated into the enantiomers by preparative HPLC (mobile phase: (isohexane/ethanol 30/70 (v/v), flow rate 15 ml/min, temperature 40° C., wavelength: 220 nm) on a chiral phase (Daicel Chiralpak AZ-H, 5 µM, 250×20 mm).

Example 1-1

Enantiomer 1

(5S)-2-{5-Fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one

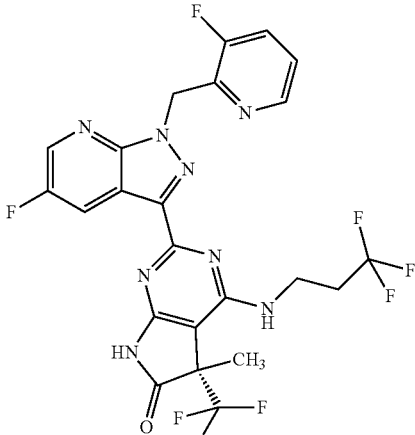

Yield: 138 mg
R$_t$=4.056 min; ee>99% [analytical HPLC, mobile phase: isohexane/ethanol 30/70 (v/v), flow rate 1 ml/min, temperature 40° C., wavelength: 220 nm, on a chiral phase (Daicel Chiralpak AZ-H, 5 µM 250×4.6 mm)].

Single crystal X-ray structural analysis confirmed the S configuration of this enantiomer.

Example 1-2

Enantiomer 2

(5R)-2-{5-Fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one

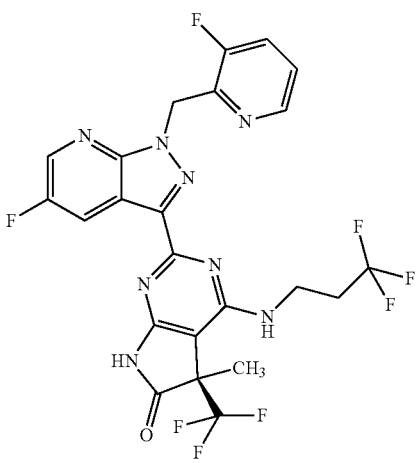

Yield: 145 mg
R$_t$=5.576 min; ee>99% [analytical HPLC, mobile phase: isohexane/ethanol 30/70 (v/v), flow rate 1 ml/min, temperature 40° C., wavelength: 220 nm, on a chiral phase (Daicel Chiralpak AZ-H, 5 µM 250×4.6 mm)].

B. ASSESSMENT OF PHARMACOLOGICAL EFFICACY

Hereinbelow, the following abbreviations are used:
BSA bovine serum albumin
EDTA ethylenediaminetetraacetic acid
µCi microcurie
Tris tris(hydroxymethyl)aminomethane
The pharmacological effect of the compounds according to the invention can be shown in the following assays:

B-1. Vasorelaxant Effect In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To produce a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. This is used to calculate the concentration needed to reduce the magnitude of the control value by 50% ($IC_{50}$ value). The standard administration volume is 5 µl; the DMSO content in the bath solution corresponds to 0.1%.

Representative $IC_{50}$ values for the compounds according to the invention are shown in the table below (Table 1):

TABLE 1

| Example No. | $IC_{50}$ [nM] |
| --- | --- |
| 1-1 | 265 |
| 1-2 | 237 |

B-2. Effect on a Recombinant Guanylate Cyclase Reporter Cell Line

The cellular activity of the compounds according to the invention is determined using a recombinant guanylate cyclase reporter cell line, as described in F. Wunder et al., *Anal. Biochem.* 339, 104-112 (2005).

Representative values (MEC=minimum effective concentration) for the compounds according to the invention are shown in the table below (Table 2):

TABLE 2

| Example | MEC [µM] |
| --- | --- |
| 1-1 | 0.1 |
| 1-2 | 1.0 |

B-3. Radiotelemetric Measurement of Blood Pressure on Conscious Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6.00 am and at 7.00 pm.

Transmitter Implantation

The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

Anaesthesia is initiated with $O_2+N_2O$ gas 30:50 with 5% isoflurane in a flow vessel.

Following initiation of anaesthesia, the anaesthesia mask is attached to the animal, which is on a warming plate, and 1.8% of isoflurane are administered for anaesthesiais maintenance. The animals are shaved and disinfected over a large area of their abdomen. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed.

Post-operatively, an antibiotic (Oxytetracyclin® 10%, 60 mg/kg s.c., 0.06 ml/100 g body weight, Beta-Pharma GmbH & Co, Germany) for infection prophylaxis and an analgesic (Rimadyl®, 4 mg/kg s.c., Pfizer, Germany) are administered.

Substances and Solutions

Unless indicated otherwise, the substances to be investigated are administered orally by gavage in each case to a group of animals (n=6). The test substances are dissolved in suitable solvent mixtures, or suspended in 0.5% strength Tylose, appropriate for an administration volume of 2 ml/kg of body weight.

A solvent-treated group of animals is employed as control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch and are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
- systolic blood pressure (SBP)
- diastolic blood pressure (DBP)
- mean arterial pressure (MAP)
- heart rate (HR)
- activity (ACT).

The acquisition of measurements is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9.00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed to be the time 2 hours before administration, and so the selected data set encompasses the period from 7.00 am on the day of the experiment to 9.00 am the following day.

The data are smoothed over a presettable time by determination of the average (30-minute average) and transferred as a text file to a storage medium. The measured values presorted and compressed in this way are transferred into Excel templates and tabulated. For each day of the experiment, the data obtained are stored in a dedicated file bearing the number of the experiment. Results and test protocols are filed sorted by numbers.

Representative values for the compounds according to the invention are shown in the table below (Table 3):

TABLE 3

Example 1-1

| hours after substance administration | Vehicle 2 ml/kg mean blood pressure (mmHg) | Dosage: 0.3 mg/kg p.o. mean blood pressure (mmHg) | Dosage: 0.03 mg/kg mg/kg mean blood pressure (mmHg) |
|---|---|---|---|
| 0 | 143.6 | 138.7 | 148.8 |
| 1 | 142.0 | 116.3 | 133.5 |
| 2 | 138.5 | 106.8 | 127.3 |
| 3 | 141.2 | 107.2 | 128.8 |
| 4 | 141.5 | 105.5 | 132.3 |
| 5 | 138.7 | 106.2 | 126.0 |
| 6 | 136.7 | 106.8 | 124.5 |
| 7 | 147.8 | 101.7 | 138.8 |
| 8 | 154.7 | 111.3 | 143.8 |
| 9 | 143.3 | 109.0 | 136.5 |
| 10 | 150.8 | 113.3 | 143.8 |
| 11 | 149.2 | 114.8 | 141.7 |
| 12 | 150.7 | 112.0 | 141.7 |
| 13 | 151.7 | 117.2 | 150.5 |
| 14 | 148.8 | 115.7 | 150.8 |
| 15 | 155.3 | 117.8 | 153.8 |
| 16 | 150.3 | 111.5 | 145.7 |
| 17 | 155.5 | 121.7 | 155.3 |
| 18 | 156.7 | 132.3 | 151.2 |
| 19 | 160.2 | 117.0 | 146.3 |
| 20 | 144.5 | 110.7 | 140.2 |
| 21 | 151.5 | 124.0 | 142.2 |
| 22 | 145.5 | 125.5 | 142.8 |
| 23 | 165.0 | 139.0 | 143.0 |
| 24 | 171.5 | 150.5 | 143.2 |

REFERENCES

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-4. Determination of Pharmacokinetic Parameters Following Intravenous and Oral Administration The pharmacokinetic parameters of the compounds of the formula (I) according to the invention are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right *Vena jugularis* externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at −20° C. until further processing.

An internal standard (which may also be a chemically unrelated substance) is added to the samples of the compounds of the formula (I) according to the invention, calibration samples and qualifiers, and this is followed by protein precipitation using excess acetonitrile. Addition of a buffer solution matched to the LC conditions, and subsequent vortexing, is followed by centrifugation at 1000 g. The supernatant is analysed by means of LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC (area under the curve), $C_{max}$, $t_{1/2}$ (terminal half life), F (bioavailability), MRT (mean residence time) and CL (clearance), using a validated pharmacokinetic calculation programme.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $C_{blood}/C_{plasma}$ value.

Table 4 shows data of representative compounds of the present invention following intravenous administration of 0.3 mg/kg and oral administration of 1 mg/kg in rats:

TABLE 4

|  | Example 1-1 |
|---|---|
| $AUC_{norm}$ [kg · h/l] | 1.77 |
| $CL_{blood}$ [l/h/kg] | 0.70 |
| MRT [h] | 6.6 |
| $t_{1/2}$ [h] | 5.9 |
| F [%] | 98.8 |

B-5. Metabolic Study

To determine the metabolic profile of the compounds according to the invention, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds according to the invention were incubated with a concentration of about 0.1-10 μM. To this end, stock solutions of the compounds according to the invention having a concentration of 0.01-1 mM in acetonitrile were prepared, and then pipetted with 1:100 dilution into the incubation mixture. Liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were quenched with acetonitrile (final concentration about 30%) and the protein was centrifuged off at about 15 000×g. The samples thus stopped were either analysed directly or stored at −20° C. until analysis.

The analysis is effected by means of high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic assessment of the compound according to the invention in the incubation mixtures.

B-6. Inhibition of Bovine Phosphodiesterase 6 (PDE 6)

PDE 6 is purified from external photoreceptor segments of bovine retina (ROS), activated by mild trypsination and purified further by ion exchange chromatography using a Mono Q column. Fractions having PDE 6 activity are combined (PDE 6 preparation) and stored at −80° (I. Saenz de Tejada et al., *International Journal of Impotence Research* 2001, 13, 282- 290). The in vitro effect of test substances on bovine PDE 6 is determined using the commercially available 3H-cGMP Scintillation Proximity Assay (SPA) from Perkin Elmer. The reaction (20 mM, 37° C.) comprises serial dilution series of the test substances in DMSO and PDE 6 preparation (typical dilution 1:100,000), [$8^{-3}$H]guanosine 3',5'-cyclic phosphate (0.25 μCi/mL; Perkin Elmer) and unlabelled cGMP (10 μM) in assay buffer (50 mM Tris/HCl pH 7.5; 140 mM NaCl; 8.3 mM $MgCl_2$; 1.7 mM EDTA; 0.02% BSA). $IC_{50}$ values are determined by plotting the substance concentration against the percent PDE 6 inhibition determined (Wunder et al. *Molecular Pharmacology* 2005, 68, 1775-1781).

Representative $IC_{50}$ values for the compounds according to the invention are shown in the table below (Table 5):

TABLE 5

| Example No. | $IC_{50}$ [nM] |
|---|---|
| 1-1 | 220 |
| 1-2 | 1400 |

B-7. Determination of Organ-Protective Effects in a Long-Term Experiment on Rats The organ-protective effects of the sGC stimulators were shown in a therapeutically relevant "low nitric oxide (NO)/high renin" hypertension model in rats. The study was conducted following a recently published article (Sharkovska Y, Kalk P, Lawrenz B, Godes M, Hoffmann L S, Wellkisch K, Geschka S, Relle K, Hocher B, Stasch J P. NO-independent stimulation of soluble guanylate cyclase reduces target organ damage in low- and high-renin models of hypertension. J. Hypertension. 2010; 28: 1666-1675). This involved treating renin-transgenic rats (TGR(mRen2)27) to which the NO synthase inhibitor L-NAME had been administered via drinking water simultaneously with an sGC stimulator or vehicle over several weeks. Haemodynamic and renal parameters were determined during the treatment period. At the end of the long-term study, organ protection (kidney, lung, heart, aorta) was shown by histopathological studies, biomarkers, expression analyses and cardiovascular plasma parameters.

C. WORKING EXAMPLES OF PHARMACEUTICAL COMPOSITIONS

The compounds according to the invention can be converted to pharmaceutical formulations as follows:

Tablet:

Composition:

100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% solution (w/w) of the PVP in water. The granules are dried and mixed with the magnesium stearate for 5 minutes. This mixture is pressed with a conventional tableting press (for tablet dimensions see above). The guide value used for the pressing is a pressing force of 15 kN.

Suspension which can be Administered Orally:
Composition:
1000 mg of the compound according to the invention, 1000 mg of ethanol (96%), 400 mg of Rhodigel® (xanthan gum from FMC, Pa., USA) and 99 g of water.
A single dose of 100 mg of the compound according to the invention corresponds to 10 ml of oral suspension.
Production:
The Rhodigel is suspended in ethanol and the compound according to the invention is added to the suspension. The water is added while stirring. The mixture is stirred for about 6 h until swelling of the Rhodigel is complete.
Solution for Oral Administration:
Composition:
500 mg of the compound according to the invention, 2.5 g of polysorbate and 97 g of polyethylene glycol 400. A single dose of 100 mg of the compound according to the invention corresponds to 20 g of oral solution.
Production:
The compound according to the invention is suspended in the mixture of polyethylene glycol and polysorbate while stirring. The stirring operation is continued until dissolution of the compound according to the invention is complete.
i.v. Solution:
The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:
1. A compound having the systematic name 2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and the structural formula (I)

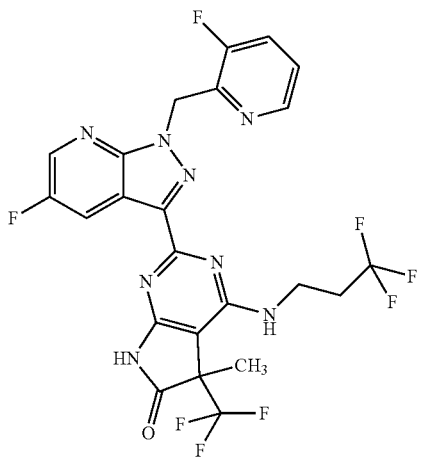

or a salt thereof.

2. An enantiomer of the compound of claim 1 having the systematic name (5R)-2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and the structural formula (I-A)

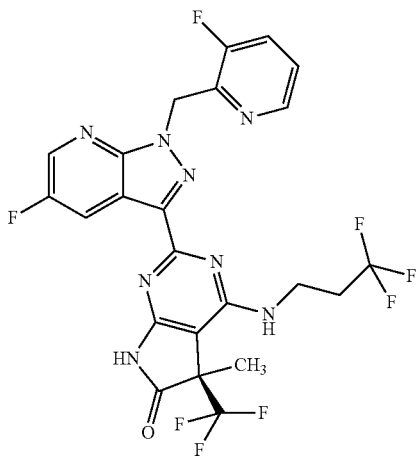

or salt thereof.

3. An enantiomer of the compound of claim 1, having the systematic name (5S)-2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one and the structural formula (I-B)

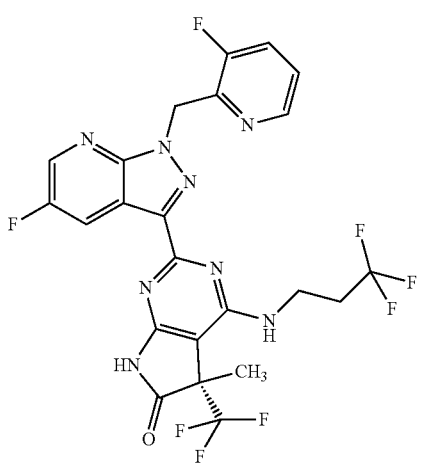 [SMILES: C[C@@]1(C(F)(F)F)C(=O)Nc2nc(-c3nn(Cc4ncccc4F)c4ncc(F)cc34)nc(NCCC(F)(F)F)c21]

or a salt thereof.

4. A pharmaceutical composition comprising a compound of claim 1 and an inert, non-toxic, pharmaceutically suitable auxiliary.

5. A pharmaceutical composition comprising a compound of claim 2 and an inert, non-toxic, pharmaceutically suitable auxiliary.

6. A pharmaceutical composition comprising a compound of claim 3 and an inert, non-toxic, pharmaceutically suitable auxiliary.

7. The pharmaceutical composition of claim 4, further comprising an active compound selected from the group consisting of an organic nitrate, an NO donor, a cGMP-PDE inhibitor, an agent having antithrombotic activity, an agent lowering blood pressure, and an agent altering lipid metabolism.

8. The pharmaceutical composition of claim 5, further comprising an active compound selected from the group consisting of an organic nitrate, an NO donor, a cGMP-PDE inhibitor, an agent having antithrombotic activity, an agent lowering blood pressure, and an agent altering lipid metabolism.

9. The pharmaceutical composition of claim 6, further comprising an active compound selected from the group consisting of an organic nitrate, an NO donor, a cGMP-PDE inhibitor, an agent having antithrombotic activity, an agent lowering blood pressure, and an agent altering lipid metabolism.

10. A process for preparing a compound of claim 1, comprising converting a compound of the formula (II)

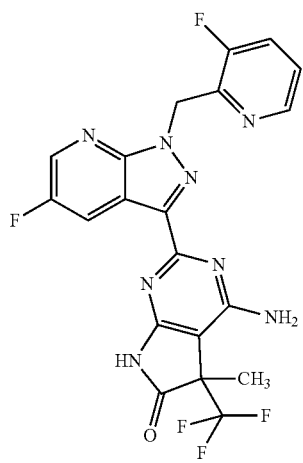

(II)

in an inert solvent using isopentyl nitrite and a halogen equivalent into a compound of the formula (III)

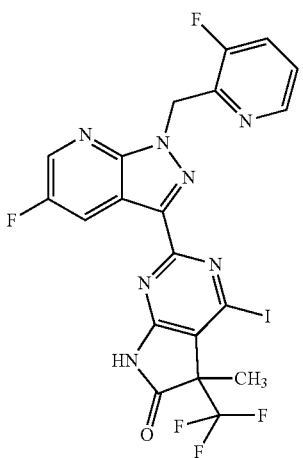

(III)

reacting the compound of formula (III) in an inert solvent, optionally in the presence of a suitable base, with a compound of the formula (IV)

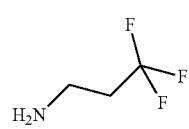

(IV)

to give a compound of the formula (I)

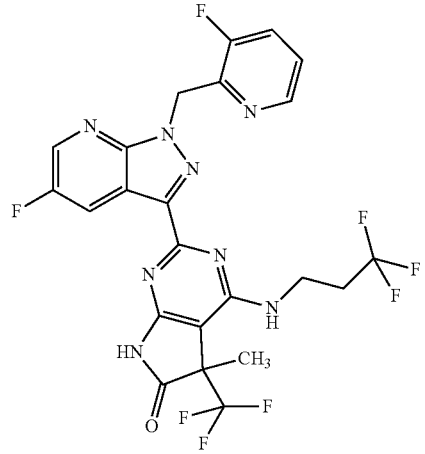

(I)

and optionally converting the compound of the formula (I) with a (i) solvent and/or (ii) acid or base into solvate, salt and/or solvate of a salt thereof.

11. The process of claim 10, further comprising separating the compound of formula (I) into enantiomers thereof.

12. A method for the treatment of heart failure, angina pectoris, hypertension, pulmonary hypertension, ischaemias, vascular disorders, renal insufficiency, thromboembolic disorders, fibrotic disorders and arteriosclerosis comprising administering to a human or animal in need thereof an effective amount of at least one compound of claim 1.

13. A method for the treatment of heart failure, angina pectoris, hypertension, pulmonary hypertension, ischaemias, vascular disorders, renal insufficiency, thromboembolic disorders, fibrotic disorders and arteriosclerosis comprising administering to a human or animal in need thereof an effective amount of at least one compound of claim 2.

14. A method for the treatment of heart failure, angina pectoris, hypertension, pulmonary hypertension, ischaemias, vascular disorders, renal insufficiency, thromboembolic disorders, fibrotic disorders and arteriosclerosis comprising administering to a human or animal in need thereof an effective amount of at least one compound of claim 3.

15. A method for the treatment of heart failure, angina pectoris, hypertension, pulmonary hypertension, ischaemias, vascular disorders, renal insufficiency, thromboembolic disorders, fibrotic disorders and arteriosclerosis comprising administering to a human or animal in need thereof an effective amount of the pharmaceutical composition of claim 4.

16. A method for the treatment of heart failure, angina pectoris, hypertension, pulmonary hypertension, ischaemias, vascular disorders, renal insufficiency, thromboembolic disorders, fibrotic disorders and arteriosclerosis comprising administering to a human or animal in need thereof an effective amount of the pharmaceutical composition of claim 5.

17. A method for the treatment of heart failure, angina pectoris, hypertension, pulmonary hypertension, ischaemias, vascular disorders, renal insufficiency, thromboembolic disorders, fibrotic disorders and arteriosclerosis comprising administering to a human or animal in need thereof an effective amount of the pharmaceutical composition of claim 6.

* * * * *